United States Patent [19]

Hashimoto et al.

[11] 4,335,211

[45] Jun. 15, 1982

[54] PROCESS FOR PRODUCING OPTICALLY ACTIVE CEPHALOSPORIN ANALOGS

[75] Inventors: Yukio Hashimoto, Yamato; Seigo Takasawa, Hadano; Tadashi Hirata, Yokohama; Ikuo Matsukuma, Yokkaichi; Shigeo Yoshiie, Sakai, all of Japan

[73] Assignee: Kyowa Hakko Kogyo Co., Ltd., Tokyo, Japan

[21] Appl. No.: 206,556

[22] Filed: Nov. 13, 1980

[30] Foreign Application Priority Data

Nov. 14, 1979 [JP] Japan .................................. 54-146489

[51] Int. Cl.³ .......................................... C12P 17/18
[52] U.S. Cl. ..................................... 435/119; 435/50; 435/874; 435/910; 435/848; 435/824; 435/830; 435/823; 435/829; 435/842; 435/843; 435/882; 435/832; 435/850; 435/840; 435/859; 435/873

[58] Field of Search .................................... 435/119, 50

[56] References Cited

U.S. PATENT DOCUMENTS 3,862,004  1/1975  Takahashi et al. ...................... 435/50
3,945,888  3/1976  Takahashi et al. ...................... 435/50

OTHER PUBLICATIONS

Guthikonda et al., J. Am. Chem. Soc., vol. 96, No. 24, pp. 7584+7585 (1974).

Primary Examiner—Alvin E. Tanenholtz
Attorney, Agent, or Firm—Fitzpatrick, Cella, Harper & Scinto

[57] ABSTRACT

Disclosed are optically active acylated cephalosporin analogs which are useful as antibacterial agents and methods for preparing such compounds.

4 Claims, No Drawings

PROCESS FOR PRODUCING OPTICALLY ACTIVE CEPHALOSPORIN ANALOGS

BACKGROUND OF THE INVENTION

The present invention relates to optically active cephalosporin analogs and, more particularly, it pertains to optically active compounds of cephalosporin analogs represented by the general formula (I)

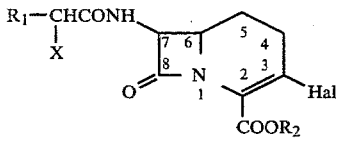

(wherein $R_1$ represents a substituted or unsubstituted, saturated or unsaturated six-membered carbocyclic or five-membered heterocyclic group, $R_2$ represents a hydrogen or a protective group of carboxylic acid, Hal represents a halogen atom, X represents a hydrogen, a lower alkyl group, a hydroxy group, a carboxyl group or an amino group and the hydrogens at the 6- and 7-positions have cis configuration), pharmaceutically acceptable salts thereof, and a process for producing the same.

The compounds represented by the general formula (I), (II), . . . may be named Compound [I], Compound [II], . . . , respectively.

Heretofore, a carbacephem compound, which is named according to the nomenclature in J. Am. Chem. Soc. 96, 7584 (1974), wherein the sulfur atom of cephalosporin is substituted with a carbon atom and which has a substituted methyl group at the 3-position is described in the above reference and J. Med. Chem. 20, 551 (1977). However, no compound having especially strong antibacterial activity has been reported.

The present inventors have succeeded in preparing carbacephem compounds having various substituents at the 4-, 5- or 3-position. The compounds are described in the specification of Japanese Patent Application (referred to as "JPA", hereinafter) No. 34696/78 [Japanese Patent Unexamined Patent Application (referred to as "JPUPA", hereinafter) No. 128591/79], JPA No. 122403/78 (JPUPA No. 49376/80), JPA No. 133072/78 (JPUPA No. 59186/80), JPA No. 162005/78 (JPUPA No. 87788/80), JPA No. 162008/78) (JPUPA No. 87791/80), JPA No. 8408/79 (JPUPA No. 100384/80), German Offenlegungsschrift No. 2911786 and U.S. Patent Application Ser. No. 023,645 now U.S. Pat. No. 4,291,164. Especially, optically inactive cephalosporin analogs are described in detail in Japanese Patent Application No. 92035/79 (U.S. Patent Application Ser. No. 171,297).

Further, novel acylated carbacephems which have strong antibacterial activities are describes in JPA No. 34696/78 (JPUPA No. 128591/79), JPA No. 122402/78 (JPUPA No. 49375/80), JPA No. 127027/78 (JPUPA No. 53290/80), JPA No. 133071/78 (JPUPA No. 59185/80), JPA No. 162006/78 (JPUPA No. 87789/80), JPA No. 162007/78 (JPUPA No. 87790/80), JPA No. 8409/79 (JPUPA No. 100391/80), JPA No. 92035/79 and U.S. Patent Application Ser. No. 23,646.

However, cephalosporin analogs mentioned above are prepared by synthetic methods using optically inactive starting compounds, and they are in principal optically inactive dl [represented by ($\pm$)] compounds.

That is, compounds represented by the general formula (III)

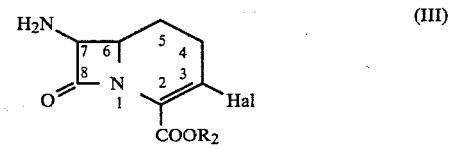

wherein $R_2$ and Hal have the same significance as defined above and the hydrogen atoms at the 6- and 7-positions have cis configuration are present as a mixture of equal amounts of the mirror image compounds represented by the formulae (III-1) and (III-2).

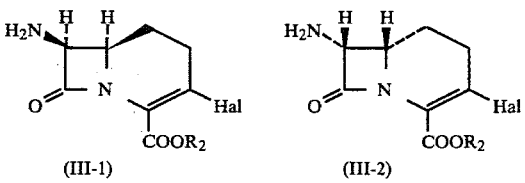

Therefore, all acyl compounds derived from such carbacephem compounds are optically inactive.

On the other hand, a compound wherein an optically active acyl group such as D-phenylglycyl group is introduced to an optically inactive carbacephem compound, for example, the compound represented by the general formula (IV)

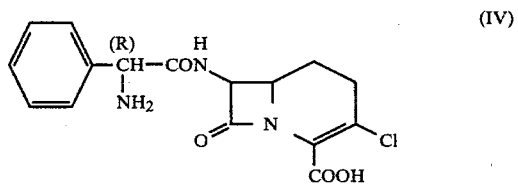

is separated to diastereoisomers (JPA No. 92035/79). The diastereoisomers are assumed to have the absolute structural formulae (IV-1) and (IV-2).

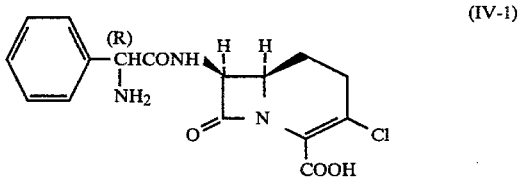

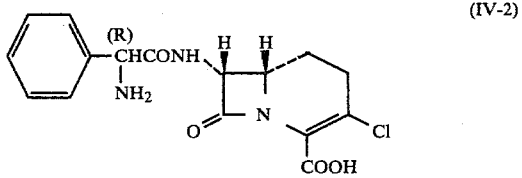

However, this method is complicated because in the preparation of Compound [IV], protection and elimination processes of amino group or carbonyl group are required.

Accordingly, there is a demand for optically active analogs and methods for production thereof. A method of producing optically active carbacephem compounds using culture broth of the same microorganism as those in the present invention or a treated matter thereof is described in JPA Nos. 14534/79 (JPUPA No. 108877/80), 14533/79 (JPUPA No. 108872/80) and 45897/79 and U.S. Patent Application Ser. No. 119,451 now U.S. Pat. No. 4,316,958 and 119,441 now abandoned. The method described in JPA Nos. 14533/79 and 14534/79 is complicated in the processes.

On the other hand, in the specification of JPA No. 45897/79, a method of producing optically active acyl derivative, for example, a compound represented by the general formula (IV-1) wherein Cl at the 3-position is H, by introducing an acyl group into the compound represented by the general formula (III) or (III-1) wherein Hal at the 3-position is H with a microorganism having an ability of acylating with optical selectivity is described.

To this end, it has now been found that the optically active compound of the cephalosporin analogs represented by the general formula (I) can be prepared using a microorganism capable of acylating with optical selectivity the compound represented by the general formula (III) or (III-1).

SUMMARY OF THE INVENTION

In accordance with the present invention, optically active acyl compounds of the cephalosporin analogs represented by the general formula (I), that is, the compounds represented by the general formula (I-1)

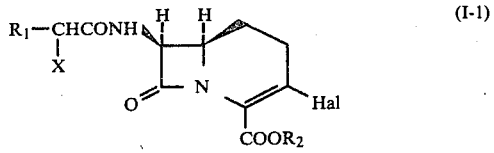

wherein $R_1$, $R_2$, X and Hal have the same significance as defined above are prepared from the compounds represented by the general formula (III) or (III-1).

Compound [III] or Compound [III-1] is acylated selectively and an α,α-disubstituted carboxylic acid represented by the general formula (II)

wherein $R_1$ and X have the same significance as defined above or a functionally equivalent reactive derivative thereof in the presence of (1) a microorganism having an ability of producing Compound [I-1] from the α,α-disubstituted carboxylic acid or reactive derivative thereof and Compound [III] or Compound [III-1] and belonging to the genus Pseudomonas, Xanthomonas, Escherichia, Aeromonas, Achromobacter, Arthrobacter, Acetobacter, Alcaligenes, Kluyvera, Gluconobacter, Clostridium, Comamonas, Corynebacterium, Sarcina, Staphylococcus, Spirillum, Bacillus, Flavobacterium, Brevibacterium, Protaminobacter, Beneckea, Micrococcus, Proteus, Mycoplana or Rhodopseudomonas, (2) a culture broth of the microorganism, (3) a treated matter of the culture broth or (4) an enzyme produced by the microorganism.

The optically active compounds obtained by the processes in Reference Examples below are assumed to have the absolute structure represented by the general formula (III-1) defined above from various properties, stronger antimicrobial activity of their acyl derivatives compared with the corresponding optically inactive dl-compound and the relationship between the absolute structure of cephalosporins and activities thereof.

In the following, the optically active compounds are described as having the absolute configuration of (6R, 7S), i.e. the configuration illustrated by the general formula (III-1) and in the following Examples and Reference Examples, the compounds are named according to the assumed absolute structural formula. It is needless to say that the optically active compounds are more useful as medicins and antimicrobial agents compared with optically inactive compounds and the compounds of the present invention are, therefore, useful as antibacterial agents which may be employed in manners well known in the art.

DETAILED DESCRIPTION OF THE INVENTION

Optically active cephalosporin analogs produced by the present invention are represented by the general formula (I-1) mentioned above.

As the unsaturated six-membered carbocyclic group and five-membered heterocyclic group $R_1$, phenyl group, cyclohexyl group, cyclohexenyl group, cyclohexadienyl group, thienyl group and furyl group are exemplified. As the substituent, hydroxy group, halogens, nitro group, amino group, methanesulfonamide group, and the like are mentioned. As the alkyl group X, straight-chain or branched alkyl groups having 1 to 5 carbon atoms such as methyl, ethyl, n-propyl, i-propyl, n-butyl, i-butyl, sec-butyl and the like are mentioned. As the halogen atom, chlorine, bromine or iodine is exemplified.

$R_2$ is a hydrogen or a protective group of carboxylic acid used in the chemistry of penicillins and cephalosporins.

As group $R_2$, the following are exemplified.

1. straight-chain or branched alkyl group having 1 to 5 carbon atoms such as methyl, ethyl, n-propyl, i-propyl, n-butyl, i-butyl, t-butyl, and the like.
2. straight-chain or branched lower alkoxymethyl group having 1 to 5 carbon atoms such as methoxymethl, ethoxymethyl, and the like.
3. straight-chain or branched halogenated alkyl group having 1 to 5 carbon atoms such as chloromethyl, 2,2,2-trichloromethyl, 2,2,2-trifluoroethyl, and the like.
4. lower alkylsulfonylethyl group such as methylsulfonylethyl, ethylsulfonylethyl, and the like.
5. arylmethyl group having 7 to 12 carbon atoms such as benzyl, diphenylmethyl, trityl, triphenylmethyl, and the like.
6. substituted silyl group such as trimethylsilyl, triphenylsilyl, and the like.
7. substituted arylmethyl group having 7 to 20 carbon atoms wherein the substituent is methoxy group, or nitro group and number of substituents on the phenyl ring is 1 to 5.
8. protective group of carboxylic acid represented by the general formula (VI)

wherein $R_4$ is a straight-chain or branched lower alkyl group having 1 to 6 carbon atoms, a straight-chain or branched lower alkoxy group having 1 to 6 carbon atoms, or a phenyl group, and $R_5$ is a hydrogen or a straight-chain or branched lower alkyl group having 1 to 6 carbon atoms.

Compound [III] used in the present invention is produced according to the method described in JPA No. 162008/78 (JPUPA No. 87791/80). Compound [III-1] is produced according to the method described in JPA No. 146488/79. A method of producing Compound [III-1] is described in detail in Reference Example below.

As the reactive derivative of Compound [II], a compound which gives Compounds [II] by the hydrolysis with a microorganism used in the present invention, a culture broth of the microorganism, a treated matter of the culture broth and/or an enzyme produced by the microorganism, such as an alkylester with methyl group, ethyl group, and the like, a thioethylester with thioglycollic acid is mentioned.

The optically selective acylation reaction of Compound [III] with Compound [II] and the acylation reaction of Compound [III-1] with Compound [II] are carried out in the presence of an enzyme obtained from a microorganism capable of producing optically active Compound [I] or Compound [I-1] by optically selective acylation of optically inactive Compound [III] or optical active Compound [III-1].

The following strains are examples of the microorganism.

| | |
|---|---|
| Aeromonas hydrophila | IFO 12634 |
| Achromobacter aceris | IFO 3320 |
| Arthrobacter simplex | ATCC 15799 |
| Acetobacter aurantius | IFO 3245 |
| Acetobacter sp. | ATCC 21760 |
| Alcaligenes faecalis | ATCC 8750 |
| Escherichia coli | ATCC 11105 |
| Escherichia coli | ATCC 13281 |
| Xanthomonas citri | IFO 3835 |
| Xanthomonas physalidicola | IFO 13555 |
| Kluyvera citrophila | ATCC 21285 |
| Gluconobacter liquefaciens | ATCC 14835 |
| Gluconobacter dioxyacetonicus | IFO 3271 |
| Clostridium acetobutylicum | ATCC 824 |
| Comamonas terrigena | IFO 12685 |
| Corynebacterium tritici | IFO 12164 |
| Sarcina lutea | ATCC 9341 |
| Staphylococcus aureus | IFO 3060 |
| Spirillum metamorphum | IFO 12012 |
| Bacillus megaterium | ATCC 14945 |
| Pseudomonas melanogenum | ATCC 17808 |
| Pseudomonas aeruginosa | IFO 3451 |
| Flavobacterium sp. | ATCC 21429 |
| Brevibacterium cerinum | ATCC 15112 |
| Protaminobacter alboflavus | IFO 13221 |
| Proteus rettgeri | ATCC 9250 |
| Beneckea hyperoptica | ATCC 15803 |
| Micrococcus luteus | AHU 1427 |
| Mycoplana bullata | IFO 13267 |
| Mycoplana dimorpha | IFO 13213 |
| Rhodopseudomonas spheroides | ATCC 21286 |

For carrying out the optically selective acylation reaction, the enzyme may be provided, more specifically, in any of the following forms:

1. As the culture liquor of the microorgnaism or treated matter thereof;
2. As cell bodies recovered from the culture broth by centrifugation which may be washed with saline water (usually about 1%), buffer solution and the like, or as a cell suspension;
3. As a disrupted cell suspension, i.e., a suspension of the cell bodies disrupted mechanically or chemically;
4. As a cell free extract, i.e., a liquid obtained by removing the disrupted cell bodies from the disrupted cell suspension; or
5. As a purified enzyme solution which is obtained by recovering the enzyme protein with ammonium sulfate from the cell free extract and subjecting the enzyme protein to gel filtration, ion-exchange cellulose column chromatography, ion-exchange Sephadex column chromatography, and the like.

Cells or the purified enzyme immobilized by a conventional method may be used.

The reaction is carried out at a temperature of 0° to 50° C., preferably 15° to 35° C. and at a pH of 5 to 8 in an inactive solvent which does not affect the reaction.

As the solvent, water is most preferably used. Organic solvents such as acetone, methanol, ethanol, N,N-dimethylformamide, dimethylsulfoxide, and the like may be used alone or in combination with water. It is effective to add phosphate buffer, Veronal buffer or citric acid buffer to control the pH in the reaction. Reaction time, which is varied according to the kind and concentration of enzymes, the kind and concentration of substrates, reaction temperature or raction pH, is generally 30 minutes to 24 hours. It is most preferable to terminate the reaction when the reaction ratio reaches maximum.

The concentration of cells is preferably 1 to 50 mg by dry weight per 1 ml of the reaction solution. When a purified enzyme is used, it is appropriate to use the amount of the enzyme having the same activity as that of the dry cell. The substrate Compound [II] is used in an amount of 0.5 to 50 mg per 1 ml of the reaction solution. Compound [III] or Compound [III-1] is used in an amount of 0.1 to 50 mg per 1 ml of the reaction solution.

When enzymes preventing the reaction such as β-lactamase, esterase, and the like are contained in the cell body, a mutant strain having a reduced productivity of the enzyme may be used. Further, inhibitors against such enzymes may be added in the reaction system to raise the reaction ratio.

After the completion of the reaction, isolation of the desired compound is carried out by a conventional method employed in the isolation and purification of organic compounds from culture liquors such as absorption using various carriers, ion-exchange chromatography, gel filtration, liquid-liquid extraction, and the like.

The invention includes within its scope pharmaceutical compositions comprising, as an active ingredient, Compound [I-1] or a pharmaceutically acceptable salt thereof in association with a pharmaceutical carrier or diluent. The compounds of this invention are administered by parenteral (intramuscular, intraperitoneal, intravenous, or subcutaneous injection routes), oral or rectal route of administration and can be formulated in dosage forms appropriate for each route of administration.

Preparations according to this invention for parenteral administration include sterile aqueous or nonaqueous solutions, suspensions, or emulsions. Examples of non-aqueous solvents or vehicles are propylene glycol, polyethylene glycol, vegetable oils such as olive oil, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for oral administration may be presented in a form suitable for absorption by the gastrointestinal tract. Tablets and capsules for oral administration may be in unit dose presentation form, and may contain conventional excipients such as binding agents, for example, syrup, acacia, gelatin, sorbitol, tragacanth, or polyvinylpyrrolidone; fillers, for example, lactose, sugar, maizestarch, calcium phosphate, sorbitol or glycine; lubricants, for example, magnesium stearate, talc, polyethylene glycol, silica; disintegrants, for example, potato starch or acceptable wetting agent such as sodium lauryl sulphate. The tablets may be coated according to methods well known in the arts. Oral liquid preparations may be in the form of aqueous or oily suspension, solution, emulsions, syrups, etc. or may be presented as a dry product, for reconstitution with water or other suitable vehicle before use. Such liquid preparations may contain conventional additive such as suspending agents, for example, sorbitol syrup, methyl cellulose, glucose sugar syrup, gelatin, hydroxyethylcellulose, carboxymethylcellulose, aluminum stearate gel, emulsifying agents, for example, lecithin or sorbitan monooleate; non-aqueous vehicles, which may include edible oils, for example, almond oil, coconut oil, propylene glycol or ethyl alcohol; preservatives, for example, methyl or propyl p-hydroxybenzoates or sorbic acid.

Compositions for rectal administration are preferably suppositories which may contain, in addition to the active substance, excipients such as cocoa butter or a suppository wax.

The dosage of active ingredient in the compositions of this invention may be varied; however, it is necessary that the amount of the active ingredient shall be such that a suitable dosage form is obtained. The selected dosage depends upon the desired therapeutic effect, on the route of administration, and on the duration of the treatment. Generally, dosage levels of between 5 to 350 mg/kg of body weight daily are administered to mammalian patients to achieve an antibiotic effect.

The present invention is explained by the following Examples.

EXAMPLE 1

Preparation of (6R, 7S) 7-(R)-phenylglycinamido-3-chloro-1-azabicyclo[4,2,0]oct-2-en-8-on-2-carboxylic acid

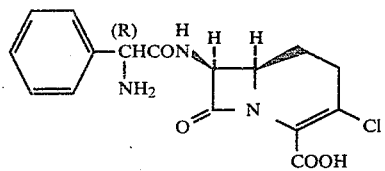

(1-1) Preparation of cell suspension (a) Cultivation of a microorganism having an ability of optically selective acylation:

As a seed strain, Pseudomonas melanogenum ATCC 17808 [Biological properties are described in Journal of the Agricultural Chemical Society of Japan 37, 71 (1963)] is used.

As the seed medium, an aqueous solution containing 1% polypepton, 1% yeast extract, 0.5% meat extract, 0.5% sodium glutamate and 0.25% sodium chloride and adjusted to a pH of 7.0 with 5 N-NaOH is used. One loopful of the seed strain is inoculated into 10 ml the seed medium in a 50 ml-large test tube and culturing is carried out at a temperature of 30° C. for 24 hours. The whole amount of the seed medium is put into 300 ml of the culture medium in a 2 l-Erlenmeyer flask and culturing is carried out at a temperature of 30° C. The composition of the culture medium is the same as that of the seed medium.

(b) Preparation of cell suspension:

After culturing for 24 hours, cell bodies are recovered from the culture broth by centrifugation and washed 2 times with 50 ml of 0.9% saline solution. The cells are suspended in a concentration of 20 mg/ml by dry weight in 1/30 M phosphate buffer (pH 6.5).

(1-2) Preparation of a substrate solution 200 mg of the trifluoroacetate of (±)-cis-7-amino-3-chloro-1-azabicyclo[4,2,0]oct-2-en-8-on-2-carboxylic acid [starting compound (a)] obtained as in the method described in JPUPA No. 87791/80 and 800 mg of the hydrochloride of D-phenylglycine methylester [starting compound (b)] are added in 9 ml of 1/30 M potassium phosphate buffer (pH 6.5). 5 N-KOH is added in a small portion and the mixture is again adjusted to a pH of 6.5 to dissolve two starting compounds. Finally, deionized water is added to make 10 ml of a solution.

(1-3) Enzyme reaction

In this step, 10 ml of the disrupted cell suspension is added to 10 ml of the substrate solution and enzyme reaction is carried out at a temperature of 30° C. for 2 hours. The reaction is monitored by high speed liquid chromatography using TRI ROTAR and Prepack column Nucleosil $10C_{18}$. Elution is carried out with 7% methanol-0.2 M $KH_2PO_4$ solution. Reaction reaches maximum in a yield of 90% to the starting compound (a) in 2 hours.

(1-4) Isolation and purification of the desired compound

After the completion of reaction, cell bodies are removed from the reaction solution by centrifugation. The supernatant is concentrated under reduced pressure and charged on a column (diameter: 1.6 cm, height: 50 cm) packed with 100 ml of Diaion HP-10. After adding 200 ml of deionized water, elution is carried out with 25% aqueous methanol solution. Then, the fractions containing the desired compound are concentrated under reduced pressure to make a 5 ml of concentrate. The concentrate is charged on a column (diameter: 1.6 cm, height: 64.5 cm) packed with 130 ml of Sephadex-LH20 and elution is carried out with a solvent of water and methanol (50:50). The desired compound is eluted in 55 ml to 75 ml of fractions. The fractions are concentrated under reduced pressure and lyophilized to obtain 78 mg of a white powder. Properties of the product coincide with the less polar isomer (A) in Reference Example 3.

Antibacterial activities of the compound obtained in Example 1 are shown in Table 1. From the antimicrobial activity, absolute configuration of this compound is assumed to be (6R, 7S).

EXAMPLE 2

Preparation of (6R, 7S) 7-[(R)-2-p-hydroxyphenyl-2-aminoacetamido]-3-chloro-1-azabicyclo[4,2,0]oct-2-en-8-on-2-carboxylic acid

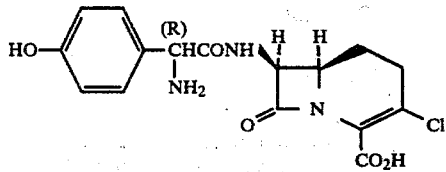

(2-1) Preparation of cell suspension Cultivation of a microorganism

The same procedure as in Example 1-1) is repeated except that as the seed strain, *Xanthomonas citri* IFO 3835 [Biological properties are described in Bergey's Manual of Determinative Bacteriology VI p. 156 (1948)] is used.

(2-2) Preparation of substrate solution 200 mg of the trifluoroacetate of (±)-cis-7β-amino-3-chloro-1-azabicyclo[4,2,0]oct-2-en-8-on-2-carboxylic acid obtained as in the method described in JPUPA No. 87791/80 and 800 mg of the hydrochloride of D-p-hydroxyphenylglycine methylester are added to 9 ml of 1/30 M potassium phosphate buffer (pH 6.5). 5 N-KOH is added in small portions and the mixture is again adjusted to a pH 6.5 to dissolve the starting compounds. Finally, deionized water is added to make 10 ml of a solution.

(2-3) Enzyme reaction and (2-4) Isolation and purification of the desired compound After the completion of the reaction, cells are removed by centrifugation and the resulting filtrate is concentrated under reduced pressure. The concentrate is charged on a column (diameter: 1.6 cm, height: 50 cm) packed with 100 ml of Diaion HP-20AG (100 to 200 mesh, product of Mitsubishi Kasei Kogyo Co., Ltd.). Then 150 ml of water and 150 ml of 10% aqueous methanol are passed through the column and elution is carried out with 20% aqueous methanol. Fractions (210 to 750 ml) of eluted 20% aqueous methanol are combined and concentrated under reduced pressure. The concentrate is charged on a column (diameter: 0.88 cm, height: 70 cm) packed with 43 ml of Sephadex LH20 (product of Pharmacia Fine Chemicals Inc.) and elution is carried out with a mixture of water and methanol (1:1, by volume). Fractions (28 to 34 ml) are combined and concentrated under reduced pressure to remove methanol. The resulting residue is lyophilized to obtain 47 mg of a white powder. The product is identified as the desired compound based on the following properties.

$[\alpha]_D^{20°} = +44.0°$ [c=0.25, 1 M phosphate buffer (pH 7.0)].

IR$\nu_{max}^{KBr}$ (cm$^{-1}$): 1765, 1695, 1615.

NMR 100 M, D$_2$O-DSS)δ: 7.36(2H, d, J=8.8 Hz), 6.96(2H, d, J=8.8 Hz), 5.36(1H, d, J=4.6 Hz), 5.11(1H, s), 3.81–4.00 (1H, m) 2.42–2.58(2H, m), 1.59–1.77 (1H, m), 1.17–1.48 (1H, m).

Antimicrobial activity of the compound obtained in this example is shown in Table 1.

EXAMPLE 3

Preparation of (6R, 7S) 7-(R)-2-phenylglycinamido-3-chloro-1-azabicyclo[4,2,0]oct-2-en-8-on-2-carboxylic acid (Alternative method)

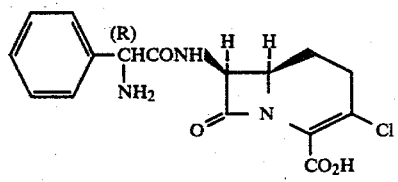

(3-1) Preparation of cell suspension (a) Cultivation of a microorganism having an ability of optically selective acylation:

As a seed strain, *Pseudomonas melanogenum* ATCC 17808 [Biological properties are described in Journal of the Agricultural Chemical Society of Japan, 37, 71 (1963)] is used.

As a seed medium, an aqueous solution containing 1% polypepton, 1% yeast extract, 0.5% meat extract, 0.5% sodium glutamate and 0.25% sodium chloride and adjusted to a pH of 7.0 with 5 N-NaOH is used. One loopful of the seed strain is inoculated into 10 ml of the seed medium in a 50 ml-large test tube and culturing is carried out at a temperature of 30° C. for 24 hours. The whole amount of the seed medium is put into 300 ml of the culture medium in a 2 1-Erlenmeyer flask and culturing is carried out with shaking at a temperature of 30° C. The composition of the culture medium is the same as that of the seed medium.

(b) Preparation of cell suspension.

After culturing for 24 hours, cell bodies are recovered from the culture broth by centrifugation and washed 2 times with 50 ml of 0.9% saline solution. The concentrate is charged on a column (diameter: 1.6 cm, height: 64.5 cm) packed with 130 ml of Sephadex-LH20 and elution is carried out with a mixture of water and methanol 50:50). The desired compound is eluted in 55 ml to 75 ml of fractions. The fractions are concentrated under reduced pressure and the residue is lyophilized to obtain 12.8 mg of a white powder. Properties of the product coincide with those of the product obtained in Example 1. The cells are suspended in a concentration of 20 mg/ml by dry weight in 1/30 M phosphate buffer (pH 6.5).

(3-2) Preparation of substrate solution 100 mg of (6R, 7S) 7-amino-3-chloro-1-azabicyclo[4,2,0]oct-2-en-8-on-2-carboxylic acid [starting compound (c)] obtained as in Reference Example 6 and 800 mg of the hydrochloride of D-phenylglycine methylester are added to 9 ml of 1/30 M potassium phosphate buffer (pH 6.5). 5 N-KOH is added in small portions and the mixture is again adjusted to a pH of 6.5 to dissolve two starting compounds. Finally, deionized water is added to make 10 ml of a solution.

(3-3) Enzyme reaction

In this step, 10 ml of the cell suspension is added to 10 ml of the substrate solution and enzyme reaction is carried out at a temperature of 30° C. for 1.5 hours. The reaction is monitored by high speed liquid chromatography using TRI ROTAR and Prepack column Nucleosil 10C$_{18}$. Elution is carried out with 7% methanol-0.2 M KH$_2$PO$_4$ solution. Reaction reaches maximum in 1.5 hours. Yield to the starting compound (c) is 90%.

(3-4) Isolation and purification of the desired compound

After the completion of reaction, cell bodies are removed from the reaction solution by centrifugation. The supernatant is concentrated under reduced pressure and charged on a column (diameter: 1.6 cm, height: 50 cm) packed with 100 ml of Diaion HP-10. After adding 200 ml of deionized water, elution is carried out with 25% aqueous methanol solution. The fractions containing the desired compound are concentrated under reduced pressure to make 5 of a concentrate. The concentrate is charged on a column (diameter: 1.6 cm, height: 64.5 cm) packed with 130 ml of Sephadex LH 20 and elution is carried out with a mixture of water and methanol (50:50). The desired compound is eluted in fractions of 55 ml to 75 ml. The fractions are concentrated under reduced pressure and lyophilized to obtain 128 mg of a white powder. Properties of the product coincide with those of the product obtained in Example 1.

EXAMPLE 4

Preparation of (6R, 7S) 7-[(R)-2-phenyl-2-aminoacetamido]-3-chloro-1-azabicyclo[4,2,0]oct-2-en-8-on-2-carboxylic acid (Alternative method)

Example (1-1) is repeated except that as the seed strain *Kluyvera citrophila* ATCC 21285 [Biological properties are described in J. General Applied Microbiology 3, 27-31 (1957)] is used. After 24 hours of the main cultivation, cells are recovered from the culture broth by centrifugation and a cell suspension is obtained by the same treatment as in Example (1-1). Preparation of a substrate solution and enzyme reaction are carried out in the same manner as in Example (1-2) and (1-3), respectively, except that reaction is carried out for 20 hours. Purification is carried out by column chromatography using HP-10 and Sephadex LH 20 as in Example (1-4). Fractions containing the desired compound are lyophilized to obtain 86 mg of a white powder. Properties of the product coincide with those of the compound in Example 1.

REFERENCE EXAMPLE 2

Preparation of (±)-cis-7-(2-t-butyloxycarbonylaminoacetamido)-3-chloro-1-azabicyclo[4,2,0]oct-2-en-8-on-2-carboxylic acid, t-butyl ester

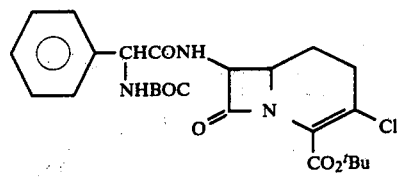

In this manner, 150 mg (0.55 mmole) of (±)-cis-7-amino-3-chloro-2-t-butyloxycarbonyl-1-azabicyclo[4,2,0]oct-2-en-8-one is dissolved in 3 ml of anhydrous methylene chloride. 166 mg (0.66 mmole) of (R)-N-t-butyloxycarbonylphenylglycine is dissolved in 5 ml of anhydrous tetrahydrofuran and the solution is cooled to −15° to −10° C. 0.66 ml (0.66 mmole) of 1N-N-methylmorpholine-tetrahydrofuran and 0.66 ml (0.66 mmole) of 1N-$^t$Bu chloroformatetetrahydrofuran are added dropwise and the mixture is stirred at the same temperature for 20 minutes. The amine solution prepared above is added dropwise to the mixture while maintaining the same temperature and temperature of the mixture is raised to room temperature gradually. The mixture is stirred at room temperature overnight. 10 ml of methylene chloride is added to the reaction mixture and the mixture is washed with 10% citric acid, saturated aqueous sodium bicarbonate and saturated aqueous sodium chloride in this order, and dried with anhydrous sodium sulfate. The mixture is concentrated under reduced pressure and purified by silica gel chromatography (silica gel; 20 g of C-200 produced by Wako Junyaku Co., Ltd., Japan solvent; ethyl acetate:n-hexane=1:5 by volume, this is same hereinafter) to obtain 124 mg (yield 44.6%) of the desired compound (mixture of the diastereoisomers) having the following properties.

IR(KBr)$\nu_{max}^{cm-1}$: 1780, 1730, 1680, 1655, 1550.

NMR (CDCl$_3$)δ(ppm): 7.34(5/2H, s), 7.31(5/2H, s), 6.93(1H, m), 5.63(1H, m), 5.30(1/2H, dd, J=5.4, 6.8

TABLE 1

| | Minimum Inhibitory Concentration (μ/ml) | | | | |
|---|---|---|---|---|---|
| Microorganism | Cefazoline | Cephalexin | The compound obtained in Example 1 | B isomer obtained in Reference Example 3 | The compound obtained in Example 2 |
| *Staphylococcus aureus* 209-P | ≦0.05 | 0.2 | 0.1 | 100 | 0.4 |
| *Staphylococcus aureus* Smith | 0.4 | 3.12 | 1.56 | >100 | 1.56 |
| *Staphylococcus epidermidis* | 0.78 | 3.12 | 1.56 | >100 | 1.56 |
| *Escherichia coli* NIHJC-2 | 1.56 | 12.5 | 1.56 | >100 | 1.56 |
| *Escherichia coli* Juhl | 1.56 | 12.5 | 1.56 | >100 | 1.56 |
| *Klebsiella pneumoniae* 8045 | 0.78 | 3.12 | 0.2 | 100 | 0.78 |
| *Klebsiella pneumoniae* Y-60 | 3.12 | 50 | 6.25 | >100 | 12.5 |
| *Serratia marcescens* T-26 | >100 | — | >100 | >100 | >100 |
| *Serratia marcescens* T-55 | 50 | 50 | 6.25 | >100 | 6.25 |
| *Proteus mirabilis* 1287 | 12.5 | 25 | 3.12 | >100 | 3.12 |

REFERENCE EXAMPLE 1

Antimicrobial activities of the compounds obtained in Examples 1 and 2 are illustrated in Table 1. Heart Infusion Agar Dilution Method (pH 7.2) is used. Cefazoline and Cephalexin are used as a control.

Hz), 5.11-5.22(3/2H, m), 3.76-3.91(1H, m), 2.33-2.66(2H, m), 1.52(9H, s), 1.41(9H, s), 0.92-1.97(2H, m).

REFERENCE EXAMPLE 3

Preparation of (6R, 7S) 7-(R)-phenylglycinamido-3-chloro-1-azabicyclo[4,2,0]oct-2-en-8-on-2-carboxylic acid (A) and (6S, 7R) 7-(R)-phenylglycinamido-3-chloro-1-azabicyclo[4,2,0]oct-2-en-8-on-2-carboxylic acid (B)

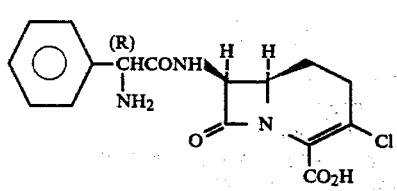
(A)

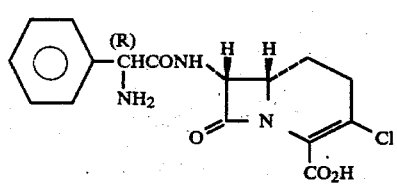
(B)

In this example, 1 ml of methylene chloride and 1 ml of trifluoroacetic acid are added to 128.4 mg (0.25 mmole) of t-butyl ester of (±)-cis-7-(2-phenyl-2-t-butyloxycarbonylaminoacetamido)-3-chloro-1-azabicyclo[4,2,0]oct-2-en-8-on-2-carboxylic acid under ice cooling and the mixture is stirred at the same temperature for 1.5 hours. The solvent is distilled off and the resultant oily material is subjected to high speed liquid chromatography [column: Microbondapak C-18 (product of Waters Co.), solvent: 7% methanol and 0.2 N KH$_2$PO$_4$] to separate diastereoisomers. Each separated eluate fraction is concentrated under reduced pressure and desalted using 10 ml of Diaion HP-10 resin (solvent; methanol: water=1:1) to obtain 9.4 mg of more polar isomer (B) and 7.6 mg of less polar isomer (A) (total yield 19.1%).

More polar isomer (B):

$[\alpha]_D^{21°}$: −75.8° (c=0.4, H$_2$O).

Melting point: 300° C. or more (browning)

IR(KBr)$\nu_{max}^{cm-1}$: 1765, 1700, 1550.

NMR(D$_2$O)δ(ppm): 7.49(5H, s), 5.16(1H, d, J=4.7 Hz), 5.05(1H, s), 3.78–4.03(1H, m), 2.53–2.67(2H, m), 1.26–2.09 (2H, m).

Less polar isomer (A):

$[\alpha]_D^{21°}$: +34.0° (c=0.35, H$_2$O).

Melting point: 300° C. or more (browning).

IR(KBr)$\nu_{max}^{cm-1}$: 1770, 1700, 1620.

NMR(D$_2$O)δ(ppm): 7.51(5H, s), 5.36(1H, d, J=4.6 Hz), 5.19(1H, s), 3.83–4.00(1H, m), 2.41–2.56(2H, m), 1.49–1.76(1H, m), 1.14–1.45(1H, m).

The less polar isomer (A) exhibits a greater antimicrobial activity and is assumed as the (6R, 7S) absolute configuration.

REFERENCE EXAMPLE 4

Preparation of (±)-cis-7-phenylacetamido-3-chloro-1-azabicyclo[4,2,0]oct-2-en-8-on-2-carboxylic acid

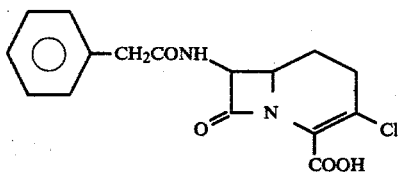

In this example, 150 mg (0.45 mmole) of trifluoroacetate of (±)-cis-7-amino-3-chloro-1-azabicyclo[4,2,0]oct-2-en-8-on-2-carboxylic acid is suspended in a mixed solvent of 2 ml of water and 2 ml of acetone, 134 mg (1.5 mmole) of sodium bicarbonate is added thereto to make a homogeneous solution. To the solution is added dropwise a solution of 84.2 mg (0.54 mmole) of phenylacetyl chloride in 0.5 ml of acetone under ice cooling in one hour. The mixture is stirred for 3 hours, adjusted to pH 2 with 1 N hydrochloric acid and extracted 5 times with each 2 ml of ethyl acetate. The extract is concentrated under reduced pressure and the residue is dried to obtain 80 mg (55.0%) of the desired compound.

IR(KBr)$\nu_{max}^{cm-1}$: 1790, 1705, 1630, 1560.

NMR(CD$_3$OD)δ(ppm): 7.29(5H, s), 5.36(1H, d, J=5 Hz), 3.79–3.99(1H, m), 2.56–2.75(2H, m), 1.17–2.02 (2H, m).

REFERENCE EXAMPLE 5

Preparation of (6R, 7S) 7-(R)-p-hydroxyphenylglycinamido-3-chloro-1-azabicyclo[4,2,0]oct-2-en-8-on-2-carboxylic acid

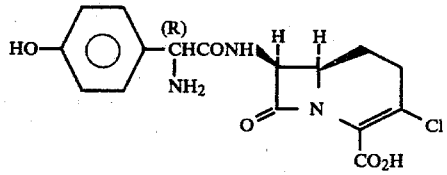

In this example, 1 ml of methylene chloride and 1 ml of trifluoroacetic acid are added under ice cooling to 104.3 mg (20 mmole) of (±)-cis-7-[2-(p-hydroxyphenyl)-2-t-butyloxycarbonylaminoacetamido]-3-chloro-1-azabicyclo[4,2,0]oct-2-en-8-on-2-carboxylic acid, t-butyl ester (mixture of the diastereoisomers) synthesized from (±)-cis-7-amino-3-chloro-1-azabicyclo[4,2,0]-oct-2-en-8-on-2-carboxylic acid, t-butyl ester and N-t-butyloxycarbonyl-(R)-p-hydroxyphenylglycine. The mixture is stirred at the temperature for 1.5 hours and concentrated under reduced pressure. The resultant oily material is subjected to high speed liquid chromatography [column: Microbondapak C-18, solvent: 7% -methanol-0.2 N potassium dihydrogen phosphate) to separate the diastereoisomers. Fractions containing the less polar isomer are concentrated under reduced pressure and desalted by 10 ml of HP-10 resin (solvent, methanol: water=1:1) to obtain 10.5 mg (28.7%) of the desired compound.

$[\alpha]_D^{20°}$: +44° (c=0.25, 1 M phosphate buffer, pH 2.5).

IR(KBr)$\nu_{max}^{cm-1}$: 1765, 1695, 1615, 1520.

NMR(D₂O)δ(ppm): 7.36(2H, d, J=8.8 Hz), 6.96(2H, d, J=8.8 Hz), 5.36(1H, d, J=4.6 Hz), 5.11(1H, s), 3.81–4.00(1H, m), 2.42–2.58(2H, m), 1.59–1.77 (1H, m), 1.17–1.48(1H, m).

REFERENCE EXAMPLE 6

Preparation of (6R, 7S) 7-amino-3-chloro-1-azabicyclo[4,2,0]oct-2-en-8-on-2-carboxylic acid (6-1) Preparation of disrupted cell suspension (1) Cultivation of a microorganism having an ability of optically selective deacylation:

As the seed strain, *Kluyvera citrophila* ATCC 21285 [Biological properties are described in J. General Applied Microbiology, 3, 28-31 (1957)] is used.

As the seed medium, an aqueous solution containing 1% polypepton, 1% yeast extract, 0.5% meat extract, 0.5% sodium glutamate and 0.25% sodium chloride and adjusted to a pH of 7.0 with 5 N-NaOH is used. One loopful of the seed strain is inoculated into 10 ml of the seed medium in a 50 ml large test tube and culturing is carried out at a temperature of 30° C. for 24 hours. The whole of the seed broth is inoculated into 300 ml of the culture medium in a 2 l-Erlenmeyer flask and culturing is carried out at a temperature of 30° C. with shaking. The composition of the main culture medium is the same as that of the seed medium.

(2) Preparation of disrupted cell suspension:

After culturing for 24 hours, the culture broth is subjected to centrifugation to obtain cell bodies. The cells are washed twice with 50 ml of 0.9% saline solution and suspended in a concentration of 40 mg/ml by dry weight in 1/30 M phosphate buffer solution (pH 8.0)

(6-2) Preparation of substrate solution

In this step, 200 mg of (±)-cis-7-phenylacetamido-3-chloro-1-azabicyclo[4,2,0]oct-2-en-8-on-2-carboxylic acid obtained as in Reference Example 4 is added to 9 ml of 1/30 M phosphate buffer (pH 8.0). Since the compound is not dissolved, 2 N-NaOH is added in a small portion and the mixture is again adjusted to a pH of 8.0 to dissolve the compound. Finally, deionized water is added to make 10 ml of a solution.

(6-3) Enzyme reaction

In this step, 10 ml of the disrupted cell suspension mentioned above is added to 10 ml of the substrate solution and enzyme reaction is carried out at a temperature of 40° C. for 80 minutes. Time course of the reaction is illustrated in Table 3.

TABLE 3

| Reaction period (minutes) | The amount of Compound (III-1) produced (mg/ml) | Yield (Mol ratio, %) |
|---|---|---|
| 10 | 1.3 | 20 |
| 20 | 1.8 | 28 |
| 40 | 2.0 | 31 |
| 60 | 2.3 | 36 |
| 80 | 2.4 | 37 |

(6-4) Isolation and Purification of the desired compound

After the completion of the reaction, cells are removed by centrifugation from the reaction solution. The supernatant is concentrated under reduced pressure to make 5 ml of solution. The solution is charged on a column (diameter: 1.75 cm, height: 42 cm) packed with Diaion HP-10. Elution is carried out with deionized water. The desired compound is eluted from 90 ml to 120 ml of the fractions. The fractions are concentrated under reduced pressure, to make 2 ml of solution and the solution is adjusted to pH 3.5 with 1 N-hydrochloric acid to deposit crystals. The crystals are recovered by filtration, washed with a small amount of methanol and dried to obtain 38 mg of a white powder. Properties of the product are as follows.

IR(KBr)$\nu_{max}^{cm-1}$: 3200, 1800, 1790(sh), 1640(sh), 1630, 1555.

NMR(100 M D₂O-DSS)δ: 4.47(1H, d, J=5.1 Hz), 3.88(1H, m), 2.64(2H, m), 1.93(2H, m).

Optical rotation $[\alpha]_D^{25°} = -2.7°$ (c=0.24, 1 M phosphate buffer, pH 7.0).

What is claimed is:

1. A process for producing optically active compounds of cephalosporin analogs represented by the formula (I)

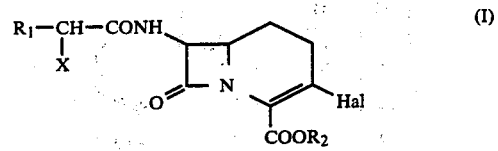

wherein $R_1$ represents a substituted or unsubstituted, saturated or unsaturated six-membered carbocyclic or five-membered hexacyclic group, $R_2$ represents a hydrogen or a protective group of carboxylic acid, Hal represents a halogen atom, the hydrogens at the 6- and 7-positions have cis configuration and X represents a hydrogen, a lower alkyl group, a hydroxy group, a carboxyl group or an amino group, which comprises reacting α,α-disubstituted carboxylic acid represented by the formula (II)

(wherein $R_1$ and X have the same significance as defined above) or a reactive derivative thereof and an optically inactive dl compound represented by the formula (III)

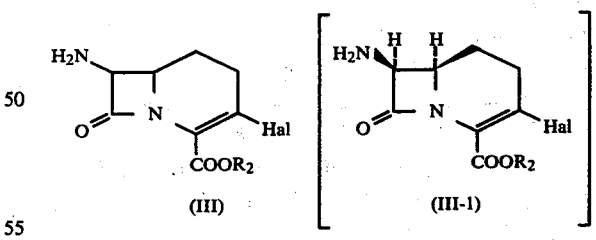

(wherein $R_2$ and Hal have the same significance as defined above) in the presence of (1) a microorganism having an ability of producing optically active compounds of the cephalosporin analog represented by the formula (I), from the α,α-disubstituted carboxylic acid or reactive derivative thereof and the compound represented by the formula (III) and belonging to the genus Pseudomonas, Xanthomonas, Escherichia, Aeromonas, Achromobacter, Arthrobacter, Acetobacter, Alcaligenes, Kluyvera, Gluconobacter, Clostridium, Comamonas, Corynebacterium, Sarcina, Staphylococcus, Spirillum, Bacillus, Falvobacterium, Brevibacterium, Protaminobacter, Beneckea, Micrococcus, Proteus, Mycoplana or Rhodopseudomonas, (2) the culture broth of said microorganism, (3) matter recovered from the culture broth of said microorganism capable of causing the production of said optically active compounds or (4) an enzyme produced by said microorganism capable of causing the production of said optically active compounds.

2. The process according to claim 1, wherein $R_1$ is a phenyl group, the substituent is a hydrogen or p-hydroxy group and X is an amino group.

3. The process according to claim 2, wherein, $R_2$ is a hydrogen, and Hal is a chlorine atom.

4. A process according to claim 1 wherein said optically active compound is converted to a pharmaceutically acceptable salt.

UNITED STATES PATENT AND TRADEMARK OFFICE
CERTIFICATE OF CORRECTION

PATENT NO. : 4,335,211

DATED : June 15, 1982

INVENTOR(S) : YUKIO HASHIMOTO, et al.

It is certified that error appears in the above-identified patent and that said Letters Patent is hereby corrected as shown below:

Column 1, line 59, "describes" should be -- described --.

Column 3, line 44, "and" should be -- with --.

line 48, "(ii)" should be -- (II) --.

Column 5, line 63, "microorgnaism" should be -- microorganism --.

Column 9, line 63, "100M" should be -- (100M, --.

Column 11, line 15, after "5" add -- ml --.

Columns 11 and 12, Table 1, in the heading, after "µ" add -- g --.

Column 12, line 4, "(±)-cis-7-(2-t-butyloxycarbonylamino-acetamido)-3-" should read -- (±)-cis-7-(2-phenyl-2-t-butyloxy-carbonylaminoacetamido)-3- --.

Column 16, lines 46 to 55, the formula in brackets should be deleted.

UNITED STATES PATENT AND TRADEMARK OFFICE
CERTIFICATE OF CORRECTION

PATENT NO. : 4,335,211

DATED : June 15, 1982

INVENTOR(S) : YUKIO HASHIMOTO, et al.

It is certified that error appears in the above-identified patent and that said Letters Patent is hereby corrected as shown below:

Column 16, line 68, "Falvobacterium" should be
-- Flavobacterium --.

Signed and Sealed this

*Twelfth* Day of *October 1982*

[SEAL]

*Attest:*

GERALD J. MOSSINGHOFF

*Attesting Officer*   *Commissioner of Patents and Trademarks*